US008802108B2

(12) United States Patent
Olsen

(10) Patent No.: US 8,802,108 B2
(45) Date of Patent: Aug. 12, 2014

(54) DIET PRODUCT COMPRISING ALGINATE

(75) Inventor: Jens Steen Olsen, Havdrup (DK)

(73) Assignee: S-Biotek Holding ApS, Copenhagen (DK)

( * ) Notice: Subject to any disclaimer, the term of this patent is extended or adjusted under 35 U.S.C. 154(b) by 266 days.

(21) Appl. No.: 12/524,235

(22) PCT Filed: Feb. 13, 2008

(86) PCT No.: PCT/DK2008/050039
§ 371 (c)(1), (2), (4) Date: Aug. 25, 2009

(87) PCT Pub. No.: WO2008/098579
PCT Pub. Date: Aug. 21, 2008

(65) Prior Publication Data
US 2010/0021495 A1    Jan. 28, 2010

Related U.S. Application Data

(60) Provisional application No. 60/939,796, filed on May 23, 2007.

(30) Foreign Application Priority Data

Feb. 13, 2007 (DK) ................................ 2007 00235

(51) Int. Cl.
*A61K 36/02* (2006.01)
*A23L 1/29* (2006.01)
*A23L 1/305* (2006.01)
*A23L 2/52* (2006.01)
*A23L 1/39* (2006.01)
*A23L 1/0532* (2006.01)
*A23J 3/14* (2006.01)

(52) U.S. Cl.
CPC .... *A23J 3/14* (2013.01); *A23L 1/29* (2013.01); *A23L 1/3055* (2013.01); *A23L 2/52* (2013.01); *A23L 1/39* (2013.01); *A23L 1/0532* (2013.01); *A23V 2002/00* (2013.01)
USPC ....................... 424/195.17; 426/573; 426/590

(58) Field of Classification Search
None
See application file for complete search history.

(56) References Cited

U.S. PATENT DOCUMENTS

| 5,324,526 | A | 6/1994 | Iwata et al. | |
|---|---|---|---|---|
| 5,342,643 | A | 8/1994 | Wolf et al. | |
| 2002/0068110 | A1 | 6/2002 | Liu et al. | |
| 2004/0228903 | A1 | 11/2004 | Te Hennepe et al. | |
| 2005/0013847 | A1 * | 1/2005 | Ballard et al. | 424/439 |
| 2005/0067726 | A1 * | 3/2005 | Yan et al. | 264/4.1 |
| 2008/0312345 | A1 * | 12/2008 | Rajsharad et al. | 514/779 |

FOREIGN PATENT DOCUMENTS

| EP | 0 493 265 A1 | 7/1992 |
|---|---|---|
| EP | 1212945 A2 | 6/2002 |
| FR | 2731588 A1 * | 9/1996 |
| JP | 2006-042816 A | 2/2006 |
| JP | 2006333803 A * | 12/2006 |
| WO | 93/08704 A1 | 5/1993 |
| WO | 9627368 A1 | 9/1996 |
| WO | 03/053169 A1 | 7/2003 |
| WO | 03053169 A1 | 7/2003 |
| WO | 2005/020717 A1 | 3/2005 |
| WO | 2005/020719 A1 | 3/2005 |
| WO | 2007056376 A2 | 5/2007 |

* cited by examiner

*Primary Examiner* — Chris R Tate
*Assistant Examiner* — Randall Winston
(74) *Attorney, Agent, or Firm* — Sughrue Mion, PLLC

(57) ABSTRACT

The present invention relates to a diet product comprising an alginate in an aqueous dissolved or swelled form at a pH value causing the alginate not to gel.

22 Claims, No Drawings

DIET PRODUCT COMPRISING ALGINATE

INTRODUCTION

The present invention relates to a composition for regulating the metabolism in humans or animals. Particularly, the invention relates to a diet product which can be used to induce loss of weight in persons in need thereof, a method for regulating food consumption, a method for regulating the diet product consumption as well as methods for regulating the levels of blood sugar or cholesterol in humans or animals.

BACKGROUND ART

Many good dietary advices exists but experience shows that it is not an easy matter to get people consuming more soluble dietary fibres even though it has long been realized, that this is beneficial to health, especially if one suffers from diabetes or obesity.

For regulating food consumption different dietary fibres are commonly used. Dietary fibres are grouped into 2 types: soluble and insoluble fibres. The insoluble dietary fibres are present in coarse bread and starchy vegetables. Examples of insoluble fibres comprise cellulose, hemicellulose, lignin and pectin. The soluble fibres are present in fruit and vegetables. Examples of soluble fibres comprise guar, dextran, alginate, starch, amylose, amylopectin, xanthan, pullulan, carrageenan and gellan.

US 2004/0228903 discloses a liquid edible composition having a pH of more than 5 and containing pectin or alginate together with a calcium salt. The calcium salt may be present in an amount exceeding its maximum solubility in the edible liquid, however it will dissolve in the stomach under the influence of the pH reduction and/or the rise in temperature. Typical calcium salts are $CaCO_3$ and $CaHPO_4$. The increasing calcium concentration will stimulate the pectin and/or alginate gellation as calcium ions and the polysaccharides form a rigid matrix. The alginate or pectin used has a viscosity below 50 cP at a shear rate of $100\ s^{-1}$.

WO 2005/020717 and WO 2005/020719 relate to a food product which in addition to alginate and insoluble calcium salt also comprises protein. The food product may be a liquid or a spoonable edible product. The alginate preferably has a molecular weight of at least $0.5 \times 10^5$ and a guluronic acid content of at least 65%.

The rigid matrix is formed when calcium ions is complexed with homogeneous blocks of guluronic acid in alginate or pectin to form an "egg box" structure. Control of the calcium concentration through out the gelling process is crucial for a uniform gel to evolve. If the initial concentration of calcium is too high the polysaccharide will precipitate rather than forming a gel. The conditions may be difficult to control in the stomach due to interpersonal differences and pre- or post-eaten food products.

Calcium-induced gelation implies that a high amount of calcium salt must be present in the product before consumption. In the drink according to US 2004/0228903, WO 2005/020717 and WO 2005/020719, the calcium salt is present as an insoluble salt. Since the drink prior to ingestion generally is desired to have a low viscosity to obtain consumer acceptance the insoluble calcium salt will precipitate during storage. Apart from the inconvenience of shaking the drink before consumption an inhomogeneous product further has the disadvantage that the consumer may not obtain the calcium salt in a proper dose for an optimal gelation to progress.

U.S. Pat. No. 5,324,526 discloses an alginate-containing food product aimed at reducing the activity of insulin to synthesize fats from glucose. The alginate is used as a dietary fibre and is produced by degradation of commercially available alginate by a certain pressure and temperature scheme. Alginates with the desired ability to reduce glucose in blood and at the same time stabilise the amount of insulin have an average molecular weight of 50.000. If the alginate is shorter, i.e. around a molecular weight of 10.000 the alginate show no tendency to reduce the blood glucose. For an alginate of a molecular weight of 100.000 the tendency to reduce blood glucose is similarly reduced compared to the alginate having a molecular weight of 50.000. Probably due to the production method, the viscosity of the alginates is low. Thus, a typical alginate of an average weight of 60.000 has at 30° C. in an aqueous concentration of 5.2-5.3% a viscosity of 13 cP.

The low viscosity results in a poor gel strength of the food product when the food product is ingested and contacted with the acid in the stomach. If the gel strength is insufficient the physiological stimulation of a feeling of satiety will not be so pronounced.

It is the object of the present invention to provide a diet product which avoids some or all of the disadvantages of the prior art. Notably, it is desired to provide a diet product which before ingestion has a viscosity low enough for consumer acceptance while at the same time when contacted with the gastric juice being able to produce a gel strength sufficient for a consumer to feel satiety.

DESCRIPTION OF THE INVENTION

The invention relates in one aspect to a diet product comprising an alginate in an aqueous dissolved or swelled form at a pH value causing the alginate not to gel.

Alginate is soluble in water and is activated by acid causing the diet product of low viscosity to become a thick gel in the stomach due to the low pH value present here. The activation of alginate by acid is of importance as it causes the fibres to have effect in the stomach and fills the stomach like a balloon. Furthermore, it is likely that the gel formed has an active function in detaining fats, thereby inhibiting their uptake in the stomach or bowels. By these means some food constituents, incl. fats, can pass undigested.

Passage through the stomach and bowels is regulated by the dietary product of the invention as a prolonged time of passage of consumed foods is observed after intake of the dietary product.

Alginate is, according to the invention, primarily used as an alkaline or alkaline earth metal, eg. sodium, lithium, potassium, calcium etc. Sodium alginate is commonly preferred due to ease of solubility and inclusion hereof on the approved list (E401). Hence, sodium alginate is approved as an additive to foods. It is widely used in foods where a thickening of the food in question is desired. Usually, this involves an activated sodium alginate in contrast to this invention, wherein a dissolved or swelled, but inactivated, sodium alginate is used, which reacts upon a lowering of the pH value as happens in the stomach. Sodium alginate can be obtained in pharmaceutical and food approved varieties. Sodium alginate originates in seaweed, especially brown seaweed from the Norwegian Sea. A particular preferred alginate has a viscosity below 800 cP in a 4% aqueous solution measured at 20° C. on a Brookfield RVT viscometer, spindle no. 2 at 20 rpm. However, to obtain a sufficient gel strength when the pH is lowered to about 2-3, the viscosity in a 4% aqueous solution measured at 20° C. on a Brookfield RVT viscometer, spindle no. 2 at 20 rpm, should be above 100 cp. Especially, alginate with a viscosity below 600 cP, in particular a viscosity between 400 and 600, is preferred. A preferred sodium alginate is sold under the name of Saltialgine™ US 20 by DEGUSSA.

Alginates are polyuronides made up of a sequence of two hexuronic acids: β-D-mannuronic acid and α-L-guluronic acid. Usually, the two sugars are not distributed at random along the chain, but sometimes form blocks of up to twenty units. The proportion of these blocks depends on the species of seaweed and whether the stripe of the balde af the seaweed is used. Less important factors are the degree of maturity, age and where the material was harvested. The ratio of mannuronic to guluronic acid (M/G) in an alginate can vary from 0.4 to 1.6. When the gelling is induced by calcium ions the gelling properties increase with higher content of guluronic acid. The present invention is, however, not particular dependent on the M/G ratio since the gelling of the alginate in the absence of calcium is caused by hydration of the polymer. In a certain aspect an M/G ratio above 1.0 is useful.

The diet product of the invention may contain a minor amount of an insoluble calcium salt to support the gelation when contacted with the gastric juice. The amount of insoluble calcium salt in the diet product usually provides less than 200 ppm calcium ions when the pH is changed to about pH=2. In a preferred aspect the amount of insoluble calcium salt in the diet product provides less than 50 ppm dissolved calcium ions when the pH is changed to about pH=2. In a preferred aspect, however, the diet product of the invention does not contain an added insoluble calcium salt. Insignificant amounts of calcium salts may be present in the tap water used for preparation of the diet product. The insoluble calcium salts may be salts formed by the combination of the calcium cation with the carbonate anion or the phosphate anion. Specific examples of insoluble calcium salts include $CaHPO_4$ and $CaCO_3$.

To obtain a sufficiently low viscosity of the diet product the molecular weight of the alginate is usually not above 150,000, more preferred not above 120,000. However, to obtain a sufficient gel strength when contacted with the gastric juice the molecular weight of the alginate is usually not below 30,000, more preferably at least 60,000.

Sodium alginate can be formulated in any aqueous solution, including pure water, almost without any addition of its own taste. In liquids such as soft drinks, squash or juice the sodium alginate can be masked to an extent where it essentially cannot be tasted or felt.

The diet product according to this invention can have any pH value not causing activation of the sodium alginate. The pH value, at which sodium alginate gels, is dependent upon origin and pre-treatment. The pH value is, in an aspect of the related invention, above 4, suitably 5 or above.

The concentration of sodium alginate in the diet product of the present invention is adjusted to meet the result desired. In a ready-to-use preparation the alginate is usually present in a concentration ranging from 0.2 to 20 g per kg, mainly 1.5 to 10 g per kg. In another embodiment the alginate is present in a concentration intended for addition to food, including beverages, before consumption.

In an aspect of the invention, insoluble calcium salts are usually not present in the diet product in substantial amounts. In aspects of the invention in which insoluble calcium salts are present, though, the amount thereof is suitably less than 1% weight based on the weight of the alginate. Preferably the amount of calcium salts is less than 0.1% weight based on the weight of the alginate.

Besides alginate, the diet product of the present invention can furthermore contain a mono- or disaccharide, eg. saccharose, glucose or invert sugar, as a mono- or disaccharide improves the solubility of alginate. The concentration of mono- or disaccharide is usually chosen depending on the concentration of alginate. According to an aspect of the invention the concentration of mono- or disaccharide is in the range of 0.1 to 60 g per kg, suitably 10 to 40 g per kg.

The alginates used in the present invention are characterised by a certain increase in the viscosity when the pH is decreased. In a certain aspect of the invention the viscosity of the diet product increased 20 times or more when the pH is lowered from around pH 7 to pH 2. In certain aspect, the increase of the viscosity is 50 times or more, such as 100 times or more. However, it is generally desired that the viscosity at low pH does not exceeds a certain threshold because it presently is believed that a too dense gel will cause an unpleasant feeling by the person ingesting the diet product. Thus, is may be desired to obtain an increase in viscosity of no more than 100 times when the pH is lowered from around pH 7 to pH 2, such an increase in viscosity of no more than 50 times.

Without being bound by theory, it is presently believed that the viscosity at pH 2 should be at least 500 cP for a sufficient effect to be obtained. Preferably, the viscosity at pH 2 is 1000 cP or more. The viscosity is generally kept below 5000 cP because an increased feeling of satiety usually is not obtained above this level. A satisfactory feeling of satiety is generally obtained at a viscosity below 2000 cP, such as below 1500 cP.

The diet product of the present invention can be produced in various embodiments. In one embodiment the diet product is a food, in another a stimulant while in a third a pharmaceutical. The diet product can be meant for cosmetic use, in which it is used in relation to a desire of loss of weight in order to improve appearance. The diet product can also be used on pathologically obese individuals in order to overcome a potentially lethal obesity.

According to an aspect of the invention the diet product is a beverage, eg. a soft drink or a soup. The diet product can be incorporated into products already on the market. This enables the opportunity of exploiting the distribution system already incorporated at i.e. producers of soft drinks, who have equipment for production and distribution all over or in parts of the world with the only change to add alginate to the product. By this means, a soft drink with a slimming effect is achieved because the intake of soluble fibres in combination with the acid content of the stomach produces a gel.

It is not decisive how the alginate is formulated and distributed. It is possible to mix the alginate with i.e. sugar in capsules with the purpose of having the consumer mixing it into a beverage or other food him- or herself. Normally, sugar is not desirable in conjunction with a diet product but considering the amount and realizing that even amounts of 1 to 2 g most often will be sufficient prior to a meal, the amount of sugar is insignificant, even for diabetics. If this is the distribution of choice, it is necessary to have the consumer mixing the ready-to-use capsules with water, if necessary flavoured, eg. squash or the like, and to carry out thorough stirring before ingestion. It is desirable to ingest an appropriate amount of liquid in order to have an optimal use of the fibres and to have an appropriate amount of gel filling the stomach. In order to have an optimal effect, one can, as an example, use 0.2 liters of liquid for a capsule containing 0.5-2.0 g of alginate.

It is assumed that the acid activated gel furthermore absorbs and detains fats thereby causing these to pass through humans undigested. Hereby, a reduced intake of calories is achieved.

It is furthermore assumed that the normal time from ingestion of a meal until the fully or partly digested food leaves the body as faeces is prolonged after ingestion of the diet product. This is an especially desirable characteristic of these fibres, which is very useful among individuals wishing to loose weight, as a reduced ingestion of food combined with a prolonged digestion in the body results in less oscillation of the blood sugar and hence a stabile feeling of satiety and well-being.

Especially diabetics will experience a significant improvement in the regulation of the blood sugar level and at the same time a loss of weight will enhance an improvement of health in the long term. Thus, the present invention also relates to the use of a method for regulating the blood sugar in a patient in need thereof, said method comprising the step of administering in a pharmaceutically effective amount a composition containing alginate in a dissolved or swelled form at a pH value not causing the alginate to gel.

The present invention also relates to a method of regulating consumption of food by ingesting the diet product at least 10 minutes prior to a main meal. Typically, ingestion will take place 10 to 30 minutes prior to a meal in order to have an accumulation of mucus in the stomach. It is well known that individuals often ingest meals too fast as the brain takes approximately 30 minutes to register filling of the stomach and elevation of the blood sugar. By means of this two-part ingestion it is achieved to have the brain aiding in a reduced ingestion of food without having the individual noticing that significantly less calories are ingested.

The invention also relates to a method of regulating ingestion of the diet product by ingesting this in an amount causing the faeces to have a density of 1 g/cm$^3$ or below, mainly 0.9 g/cm$^3$. The density of faeces is found by registering whether the faeces float in the toilet or not. Use of this diet product in a proper way will lead to floating faeces. This is very important as an indicator of proper use. The reduction in faecal density is caused because it partly contains swelled or soluble fibres in form of the activated gel. By this means, individuals can themselves regulate the ingestion of a proper amount of diet product by examining the behaviour of their faeces in water.

The daily amount of fibres ingested before a main meal is individual. An individual weighing 200 kg ingests significantly more calories than an individual weighing 90 kg and the stomach of an individual weighing 200 kg is likewise significantly larger than in an individual weighing 90 kg. Therefore, an individual weighing 200 kg needs to ingest more of the diet product than an individual weighing 90 kg. Everybody can on their own find the optimal amount by studying their faeces as described earlier.

EXAMPLES

Example 1

A man aged 41 and weighing 113 kg was treated with a diet product comprising 2.5 g of alginate (Satialgine US 20) dissolved in 0.25 liters of sugar free orange soft drink from Tuborg. The diet product was ingested once a day 15 minutes prior to dinner. After one month of treatment a loss of weight of 3.5 kg was observed. A prolonged feeling of satiety and well-being was achieved.

Example 2

A man aged 24 and weighing 140 kg was treated with a diet product as described in example 1. The diet product was ingested once a day 15 minutes prior to dinner. After one month of treatment a loss of weight of 6.5 kg was observed. A prolonged feeling of satiety and well-being was achieved.

Example 3

A woman aged 47 and weighing 56 kg was treated with a diet product comprising 1 g of alginate (Satialgine US 20) dissolved in 0.25 liters of sugar free orange soft drink from Tuborg. The diet product was ingested once a day 15 minutes prior to dinner. By this means, food intake was halved yet still achieving the same feeling of satiety as after a regular main meal. The following day, the dose was raised to 2 g causing a lack of desire to eat the main meal.

Example 4

A woman aged 49 and weighing 125 kg was treated with a diet product comprising 2.5 g of alginate (Satialgine US 20) dissolved in 0.4 liters of redcurrant juice without added sugar from COOP. The diet product was ingested 30 minutes prior to dinner causing only half of the normal amount of food to be ingested. Days 2 and 3, the amount of food ingested was only 40% of normal. The woman described, that the normal urge for sweets before bedtime was absent.

Example 5

A stock solution was prepared by dissolving 5 g Satialgine US 20 in 1 l of water. While stirring the stock solution the components indicated below for each drink were added.

| Orange drink: | |
|---|---|
| Stock solution | 250 ml |
| Aspartam, 1% aq. | 15 g |
| Orange flavour[1] | 0.8 g |
| Beta-caroten, 0.1% in plant oil | 0.3 g |
| Carmin colour, 8.2% aq. | 0.0001 g |

[1]Natural flavour preparation in ethanol.

| Lemon drink | |
|---|---|
| Stock solution | 250 ml |
| Aspartam, 1% aq. | 15 g |
| Lemon emulsion | 0.4 g |
| Green colour[2] | 0.04 g |

[2]Quinolin yellow (E104) 2.0% and Green S (E 142) 0.17%.

| Passion fruit drink | |
|---|---|
| Stock solution | 250 ml |
| Aspartam, 1% aq. | 15 g |
| Passion fruit flavour[3] | 0.2 g |
| Beta-caroten, 0.1% in plant oil | 0.3 g |
| Carmin colour, 8.2% aq. | 0.0001 g |

[3]Natural passion fruit flavours in propylene glycol (E 1520) and triacetin (E 422).

| Cola drink | |
|---|---|
| Stock solution | 250 ml |
| Aspartam, 1% aq. | 15 g |
| Cola flavour[4] | 0.8 g |
| Braun colour[5] | 0.2 g |

[4]Natural cola flavours in propylene glycol (E 1520)
[5]Ammoniated caramel (E 150d), 80% aq.

Example 6

Preparation of a Solution of Alginate and Gelation Thereof 4 g sodium alginate (S20 obtainable from Cargill) was dissolved in 1000 ml of deionised water to produce a 0.4% w/w. The viscosity was measured by a Brookfield LV viscometer, spindle N° 2, 20 rpm. At a temperature of 22° C. the pH was measured a Philips PW 9420/1 pH meter having the electrode Metrohm 6.0233.100 to 6.89. The viscosity was measured to 35.75 cP.

The pH was then decreased to pH 1.97 using 30 w/w hydrochloric acid. The gelled alginate was treated with ultra sound to removed entrapped air bubbles. The viscosity was measured to 1150 cP.

Example 7

Preparation of a Solution of Alginate and Gelation Thereof 8 g of a test alginate (XPU-LVG500 506/08 obtainable from Cargill) was dissolved in 1000 ml deionised water. The pH of the solution was 7.21. The viscosity was measured to 32.5 cp using the method described in example 6. The solution was acidified using 30 w/w hydrochloric acid to pH 2.09. After removal of the majority of the bubbles by ultra sound, the viscosity was measured to 3200 cP.

The invention claimed is:

1. A beverage or drink product comprising an alginate in an aqueous dissolved or swelled form, wherein the pH of the beverage or drink product is pH 5 or more so as to not cause the alginate to gel, wherein the alginate is present at a concentration of 0.2 to 20 g per kg of the beverage or drink product, and wherein the viscosity of the alginate increases to 20 times or more when the pH is decreased from pH 7 to pH 2.

2. The beverage or drink product according to claim 1, wherein the molecular weight of the alginate is 150,000 or below.

3. The beverage or drink product according to claim 1, wherein the alginate has a viscosity in a 4% aqueous solution not exceeding 800 cP, measured at 20° C. on a Brookfield RV viscometer, spindle N° 2, 20 rpm.

4. The beverage or drink product according to claim 1, wherein the alginate has a viscosity in a 4% aqueous solution between 100 and 800 cP, measured at 20° C. on a Brookfield RV viscometer, spindle N° 2, 20 rpm.

5. The beverage or drink product according to claim 4, wherein the alginate has a viscosity in a 4% aqueous solution between 200 and 600 cP, measured at 20° C. on a Brookfield RV viscometer, spindle N° 2, 20 rpm.

6. The beverage or drink product according to claim 1, further comprising an insoluble calcium salt, wherein the amount of insoluble calcium salt in the beverage or drink product provides less than 200 ppm calcium ions when the pH is changed to pH 2.

7. The beverage or drink product according to claim 6, wherein the amount of insoluble calcium salt in the beverage or drink product provides less than 50 ppm dissolved calcium ions when the pH is changed to pH 2.

8. The beverage or drink product of claim 1, wherein the alginate is present at a concentration of 1.5 to 10 g per kg of the beverage or drink product.

9. The beverage or drink product according to claim 1, wherein the viscosity of the beverage or drink product increases 50 times or more when the pH is decreased from pH 7 to pH 2.

10. The beverage or drink product according to claim 1, wherein the viscosity of the beverage or drink product increases 100 times or more when the pH is decreased from pH 7 to pH 2.

11. The beverage or drink product according to claim 1, further comprising an insoluble calcium salt, wherein the amount of insoluble calcium salt is present in an amount of less than 1% weight based on the weight of the alginate.

12. The beverage or drink product according to claim 1, wherein the beverage or drink product further contains a mono- or disaccharide in a concentration of 0.1 to 60 g per kg, preferably 10 to 40 g per kg.

13. The beverage or drink product according to claim 12, wherein the mono- or disaccharide is selected from the group consisting of saccharose, glucose, invert sugar or mixtures thereof.

14. The beverage or drink product according to claim 1, which is a beverage.

15. The beverage or drink product according to claim 1, which is a soft drink.

16. The beverage or drink product according to claim 1, wherein the alginate is sodium alginate.

17. The beverage or drink product according to claim 1, wherein it is present in a concentrated state.

18. A method for regulating consumption of foods in a subject in need thereof comprising the step of the subject consuming an effective amount of the beverage or drink product according to claim 1 at least 10 minutes prior to a main meal.

19. A method for regulating consumption of the diet product in a subject in need thereof comprising the step of the subject consuming the beverage or drink product according to claim 1 in such amounts that the faeces has density of 1 g/cm$^3$ or below.

20. The method according to claim 19, wherein the faeces has a density of 0.9 g/cm$^3$ or below.

21. A method for regulating the blood sugar in a subject in need thereof comprising administering to the subject a pharmaceutically effective amount of the beverage or drink product according to claim 1.

22. A method for lowering the level of cholesterol in a subject in need thereof, comprising administered to the subject a pharmaceutically effective amount of the beverage or drink product according to claim 1.

* * * * *